United States Patent [19]

Kenna

[11] Patent Number: 4,528,980
[45] Date of Patent: Jul. 16, 1985

[54] ACETABULUM SIZER AND DRILL GUIDE

[75] Inventor: Robert V. Kenna, Saddle River, N.J.

[73] Assignee: Howmedica, Inc., New York, N.Y.

[21] Appl. No.: 543,207

[22] Filed: Oct. 19, 1983

[51] Int. Cl.³ .............................................. A61F 5/04
[52] U.S. Cl. ............................ 128/92 EB; 128/92 E; 128/303 R
[58] Field of Search .............. 128/92 R, 92 E, 92 EB, 128/303 R

[56] References Cited

U.S. PATENT DOCUMENTS

| | | | |
|---|---|---|---|
| 2,725,053 | 11/1955 | Bambara et al. | 128/92 EB |
| 3,815,590 | 6/1974 | Deyerle | 128/92 EB |
| 3,859,992 | 1/1975 | Amstutz | 128/303 R |
| 4,135,517 | 1/1979 | Reale | 128/303 R |
| 4,305,394 | 12/1981 | Bertuch, Jr. | 128/303 R |
| 4,349,017 | 9/1982 | Sayegh | 128/92 EB |
| 4,433,686 | 2/1984 | Charnley | 128/303 R |
| 4,475,549 | 10/1984 | Oh | 128/303 R |

FOREIGN PATENT DOCUMENTS 2908221  9/1979  Fed. Rep. of Germany ... 128/303 R

OTHER PUBLICATIONS

Zimmer Catalog, 1978, pp. A-12, 14, 26, 27, 34, 42, 50, 60, re. acetabular devices, (Warsaw, Ind.).

*Primary Examiner*—C. Fred Rosenbaum
*Assistant Examiner*—C. W. Shedd
*Attorney, Agent, or Firm*—Charles J. Knuth; Peter C. Richardson; Harold W. Ordway

[57] ABSTRACT

An acetabulum sizer and drill guide for use in implanting an acetabular cup prosthesis comprises a substantially hemispherical shell having an outside surface that generally conforms to the outside surface of the prosthesis to be fitted into a prepared acetabulum. Viewing ports in the shell enable visual inspection of the acetabulum during sizing thereof. A circular peripheral rim on the shell is generally flush with the peripheral boundary of a properly sized acetabulum when the shell is seated therein. Drill guide structure on the shell functions to guide a drill bit into the pelvis bone adjacent the acetabulum in preparing the acetabulum for the acetabular cup prosthesis. A handle is releasably connected to the drill guide structure for manipulating the shell during sizing and drilling.

22 Claims, 10 Drawing Figures

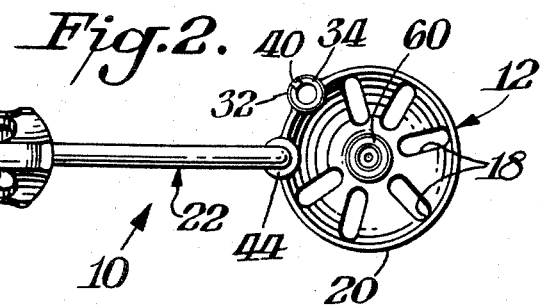
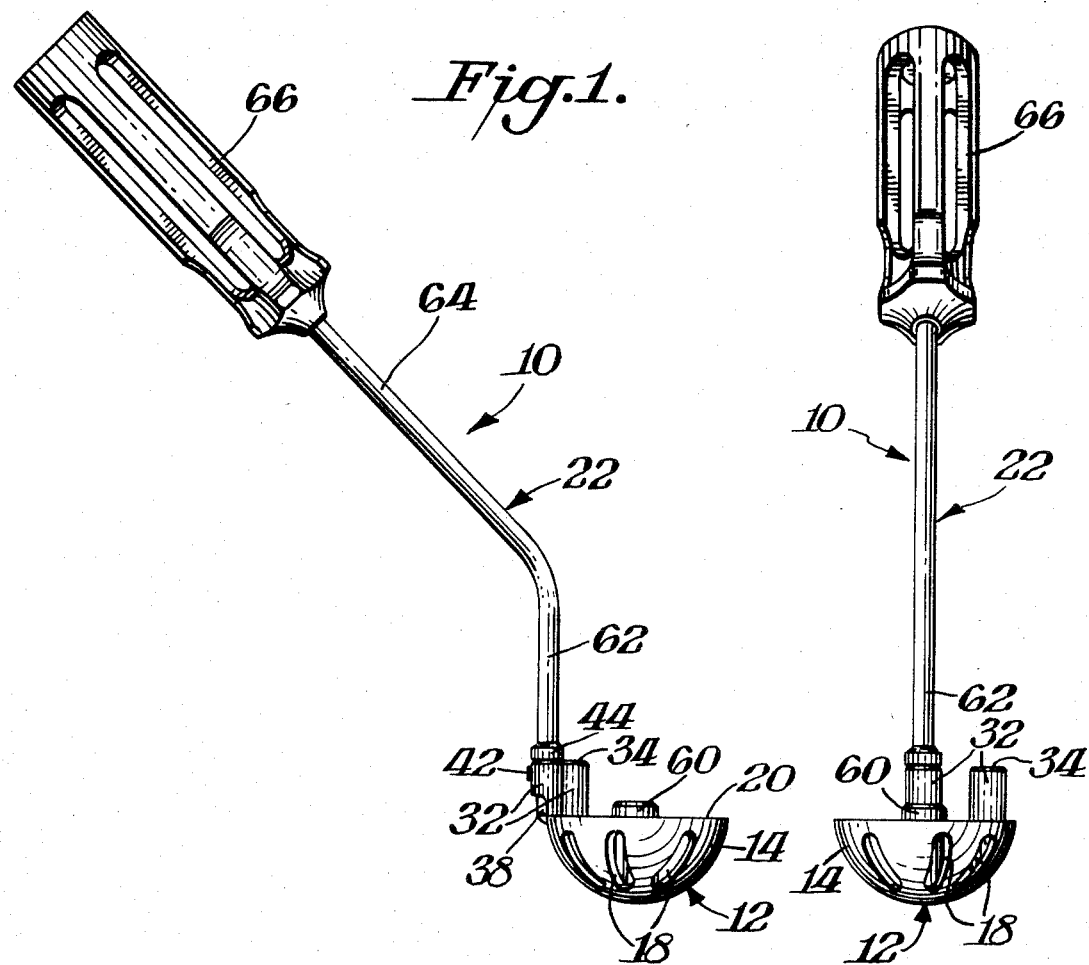
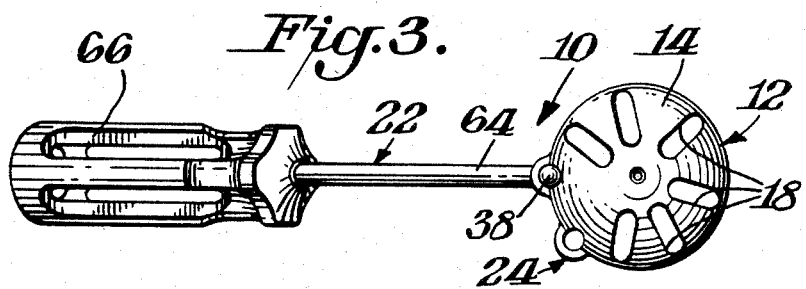

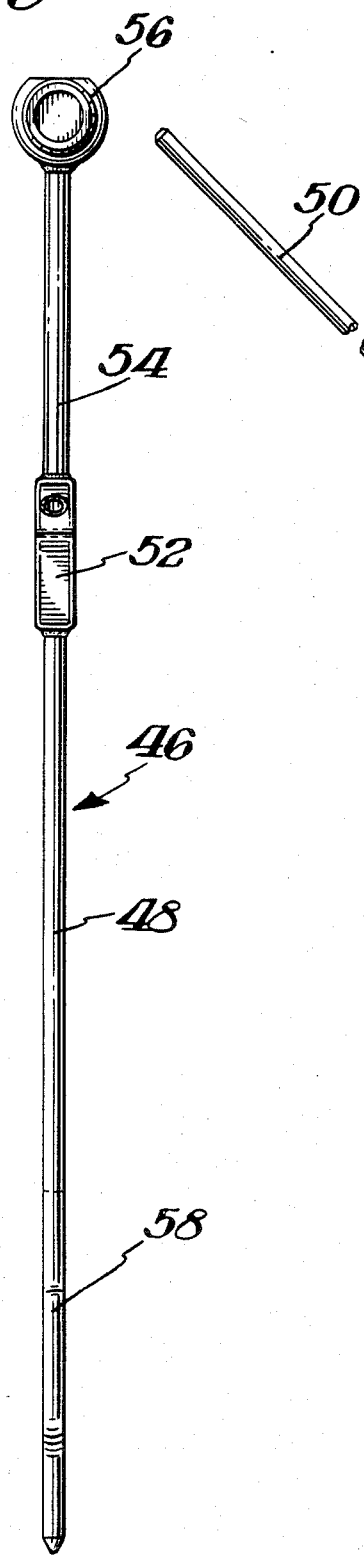
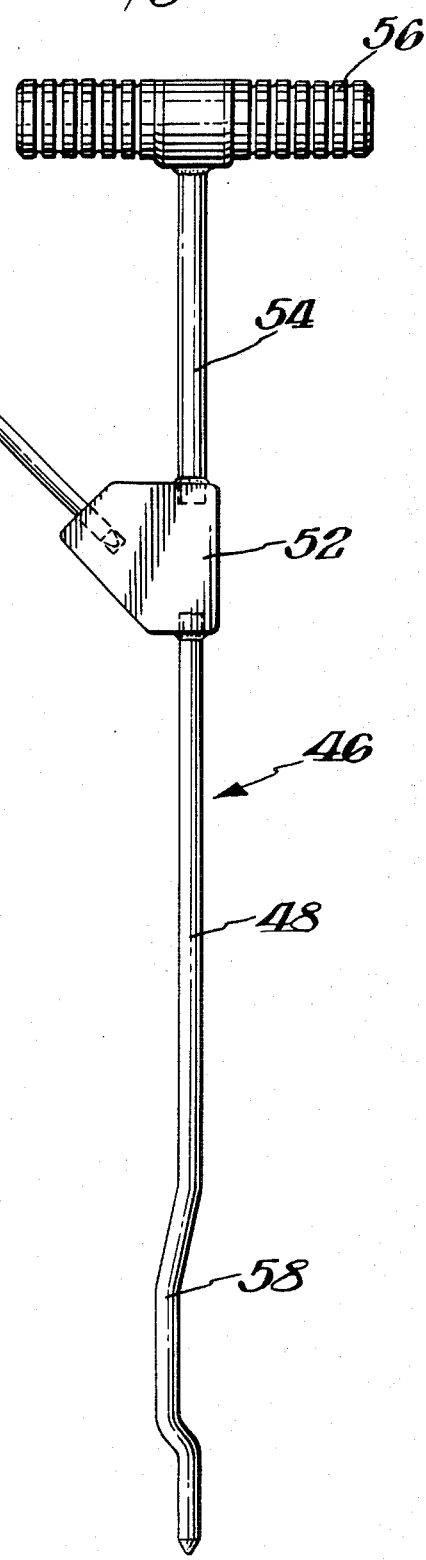

ACETABULUM SIZER AND DRILL GUIDE

BACKGROUND OF THE INVENTION

The present invention generally relates to artifical hip joints, and more particularly to acetabulum sizer and drill guide instrumentation for use in preparing an acetabulum prior to receiving an acetabular cup prosthesis.

Total hip arthroplasty includes replacement of the diseased acetabulum with an acetabular cup prosthesis, numerous arrangements having been proposed for this purpose. Following dislocation of the anatomical femoral head from its associated acetabulum, the acetabulum is prepared to receive the acetabular cup prosthesis by initially reaming the acetabulum until it dimensionally complements the prosthesis. Often it is extremely difficult to judge the amount of tissue and bone to be removed in the reaming operation in order to insure that the prosthesis properly fits within the prepared cavity. Hence there is a real need for instrumentation that assists the orthopedic surgeon in preparing the acetabulum so that it is properly sized to receive the prosthesis.

Moreover, it is often necessary to provide holes in the adjoining pelvis bone to anchor the prosthesis. The location of these holes is critical, since the final position of the prosthesis is determined by the location and angular orientation of the hole. Instrumentation is needed to insure that the anchoring holes are properly located.

SUMMARY OF THE INVENTION

Accordingly, an object of the present invention is an acetabulum sizer for properly sizing an acetabulum prior to receiving an acetabular cup prosthesis, the sizer being simple in construction and easy to use.

Another object of the present invention is a drill guide for use in forming anchoring holes in the pelvis bone that serve to precisely position the prosthesis.

Still another object of the present invention is a method of properly sizing an acetabulum prior to implantion of an acetabular cup prosthesis and forming anchoring holes in the pelvis bone that precisely position the prosthesis when implanted.

In accordance with the present invention, an acetabulum sizer for use in implanting an acetabular cup prosthesis comprises a substantially hemispherical shell having an outside surface that generally conforms to the outside surface of the prosthesis. The shell has a circular peripheral rim which is flush with a properly sized acetabulum when the shell is positioned therein. Viewing ports in the shell enable visual inspection of the acetabulum while the shell is seated therein. Handle structure is provided for manipulating the shell relative to the acetabulum.

The acetabulum sizer may include drill guide structure on the shell for guiding a drill bit into the pelvis bone adjacent the acetabulum. Specifically, the drill guide structure may include a pair of spaced apart open ended bushings on the shell close to the periphery thereof. Each bushing defines a path of travel for the drill bit and each path is perpendicular to a plane defined by the peripheral rim of the shell. When the acetabular cup prosthesis has anchoring posts spaced 45° apart, the bushings are also spaced 45° apart. Moreover, the outer end of each of the bushings serves as a stop that cooperates with the drill bit for limiting the depth of the holes drilled into the pelvis bone.

Preferably, the handle structure for manipulating the shell is releasably connected to the drill guide structure. In this regard, the handle structure may include a tip end portion constructed and arranged to releasably fit within either one of the bushings comprising the drill guide structure. Moreover, each bushing includes an open ended slot, and a key on the outside of the tip end portion of the handle structure mates within the slot when the handle is fitted into one of the bushings. This overall structural relationship properly positions the handle structure relative to the shell and prevents relative rotation.

An alignment rod is provided for properly positioning the drill guide structure relative to the acetabulum and surrounding pelvis bone. Specifically, the alignment rod has a first portion constructed and arranged for attachment to the shell, and a second portion connected to the first portion so that the axis of the second portion forms an angle of 45° with a plane defined by the circular peripheral rim of the shell. The shell is positioned within a 45° lateral opening in the acetabulum at neutral anteversion when the second portion of the alignment rod extends laterally relative to the patient and is perpendicular to the coronal axis of such patient.

Preferably, an outwardly extending socket is secured to the inside of the shell for receiving the first portion of the alignment rod. Also, the handle structure includes a proximal end portion having an axis perpendicular to a plane defined by the circular peripheral rim of the shell, a distal end portion connected to the proximal end portion at an angle of 135°, and grip means on the distal end portion.

The invention herein additionally includes a method of preparing an acetabulum prior to implanting the prosthesis therein. Bone and tissue are removed from the acetabulum until it is properly sized. Periodically, the shell is positioned within the acetabulum and the acetabulum is viewed through the ports in the shell. Determining whether the acetabulum is properly sized is accomplished by comparing the peripheral rim of the shell with the peripheral boundary of the acetabulum, the acetabulum being properly sized when the peripheral rim of the shell is generally flush with the peripheral boundary of the acetabulum. Prosthesis anchoring holes are formed in the bone surrounding the acetabulum by guiding a hole-forming tool into the bone at an angle perpendicular to the plane defined by the peripheral rim of the shell.

BRIEF DESCRIPTION OF THE DRAWING

Novel features and advantages of the present invention in addition to those mentioned above will become apparent to those skilled in the art from a reading of the following detailed description in conjunction with the accompanying drawing wherein:

FIG. 1 is a left side elevational view of an acetabulum sizer and drill guide instrument, according to the present invention;

FIG. 2 is a top plan view of the instrument;

FIG. 3 is a bottom plan view of the instrument;

FIG. 4 is a front elevational view of the instrument;

FIG. 8 is a front elevational view of an alignment rod for use with the acetabulum sizer and drill guide instrument;

FIG. 9 is a right side elevational view of the alignment rod; and

DETAILED DESCRIPTION OF THE INVENTION

Figure 5:
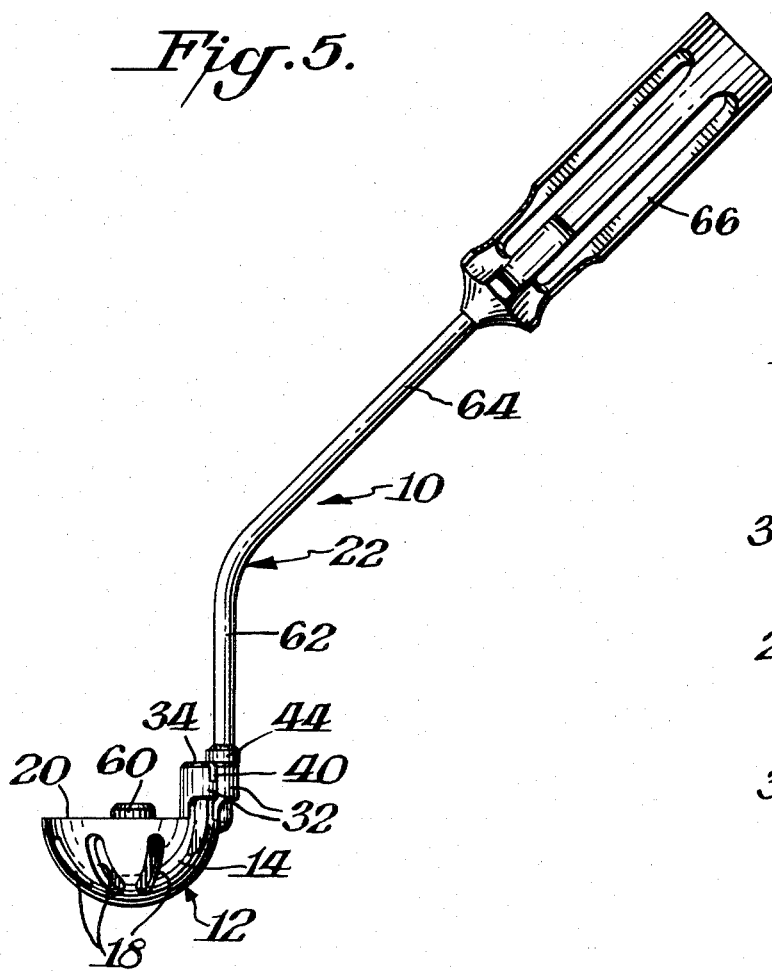
FIG. 5 is a right side elevational view of the instrument.

Referring in more particularity to the drawing, an acetabulum sizer and drill guide instrument 10 comprises a substantially hemispherical shell 12 having an outside surface 14 that generally conforms to the outside surface of an acetabular cup prosthesis (not shown) to be fitted into a prepared acetabulum 16. Viewing ports 18 are provided in shell 12 for visual inspection of the acetabulum 16 while the shell 12 is seated therein. Viewing ports 18 may comprise a series of spaced apart slotted openings positioned around shell 12. A circular peripheral rim 20 on shell 12 is generally flush with the peripheral boundary of a properly sized acetabulum 16 when shell 12 is seated therein. Handle structure 22 is provided for manipulating shell 12 relative to acetabulum 16. Instrument 10 may be fabricated from stainless steel by techniques known in the art, it being understood that other materials are equally suitable.

Instrument 10 also includes specific drill guide structure 24 for guiding a drill bit 26 into the pelvis bone 28 adjacent acetabulum 16 in the formation of prosthesis anchoring holes 30. The drill guide structure 24 comprises a pair of spaced apart open ended bushings 32 on shell 12 close to the peripheral boundary thereof. Each bushing 32 defines a path of travel for drill bit 26 which is substantially perpendicular to the plane defined by peripheral rim 20 of shell 12.

At this point, it should be pointed out that the dimensional characteristics of the particular acetabular cup prosthesis to be fitted into the acetabulum 16 dictate the dimensions of the instrument 10 of the present invention. As noted above, the outside surface 14 of shell 12 corresponds to the outside surface of the prosthesis. Additionally, the location and specifics of drill guide structure 24 are dictated by the number and location of the anchoring posts on the prosthesis. These posts fit into anchoring holes 30 formed by the interaction of drill bit 26 and bushings 32. In essence, instrument 10 is initially used by the orthopedic surgeon to determine that prepared acetabulum 16 is properly sized; after that determination is made, the instrument 10 serves to form anchoring holes 30 in the most desirable area of pelvis bone 28 surrounding acetabulum 16 whereby the prosthesis is properly fitted into the acetabulum 16 when introduced.

Bushings 32 on shell 12 are spaced 45° apart. Also, as shown best in FIG. 6, the outside upper or stop surface 34 of each bushing 32 functions as a stop for limiting the depth of the holes 30 drilled into pelvis bone 28. In this regard, drill bit 26 includes an enlarged annular collar 36 fixed to the shank of drill bit 26, and the collar 36 engages stop surface 34 of bushing 32 to thereby limit the depth of the hole 30.

Figure 6:
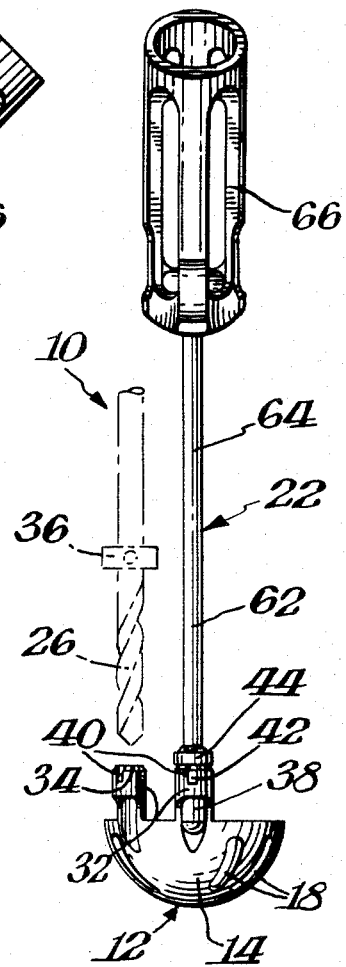
FIG. 6 is a rear elevational view of the instrument showing a drill bit in phantom outline about to enter the drill guide.
Figure 7:
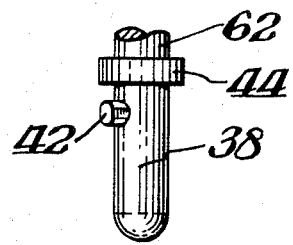
FIG. 7 is a fragmental pictorial view of the inner tip of the handle structure.

As shown best in FIGS. 6 and 7, handle 22 includes a tip end portion 38 dimensionally arranged to releasably fit within either one of bushings 32. Each bushing 32 has an open ended slot 40, and a key 42 on the outside of tip end portion 38 slidably engages within slot 40 when handle 22 is fitted into either one of bushings 32. Moreover, tip end portion 38 includes a stop 44 which limits the extent to which handle 22 is inserted into either one of bushings 32. Bottoming out of key 42 in slot 40 also serves in limiting movement of handle 22 into bushing 32. Relative rotation between handle 22 and shell 12 is prevented by the interaction between key 42 and slot 40.

An alignment rod 46 is used to assist in properly orienting the drill guide structure 24 relative to acetabulum 16 and surrounding pelvis bone 28. As shown best in FIGS. 8–10, alignment rod 46 has a first portion 48 for attachment to shell 12, as explained more fully below. A second portion 50 is releasably connected to first portion 48 by a connector block 52. Second portion 50 forms an angle of 135° with first portion 48, and, as explained more fully below, when alignment rod 46 is connected to shell 12, second portion 50 forms an angle of 45° with a plane defined by the peripheral rim 20 of the shell 12. First portion 48 of alignment rod 46 includes an extension 54 with a grip 56 at the free end thereof. Both the first portion 48 and its extension 54 are permanently fixed to connector block 52, while second portion 50 is releasably secured to connector block 52. An offset 58 near the inner end of first portion 48 provides clearance for the anatomical femur during the sizing procedure, as explained below.

As shown best in FIGS. 1 and 2, shell 12 has an outwardly extending central socket 60 for attaching alignment rod 46 to shell 12. Socket 60 may be integrally formed with shell 12 so that the central axis of socket 60 is substantially perpendicular to the plane defined by peripheral rim 20 of shell 12.

In addition to its tip end portion 38, handle 22 includes a proximal end half 62 having an axis substantially perpendicular to a plane defined by peripheral rim 20 of shell 12 when handle 22 is fitted into either bushing 32. Also, a distal half 64 is connected to proximal half 62 at an angle of approximately 135°, and a grip 66 is fixed at the end of distal half 64. The relative orientation of distal half 64, key 42 and each slot 40 is such that distal half 64 of handle 22 is angled away from shell 12 when handle 22 is fitted into either of bushings 32. This relationship provides an unobstructed view of shell 12 during the sizing and drilling procedures.

The acetabulum sizer and drill guide instrument 10 of the present invention is used in the following manner. After dislocation of the anatomical femoral head from its associated acetabulum, the acetabulum is prepared to receive the prosthesis by reaming the cavity 16 until it dimensionally complements the prosthesis. Throughout the reaming operation, the reaming tool is periodically removed and instrument 10 is positioned within the cavity 16 via manipulation of handle 22, which may be placed in either one of bushings 32 during this procedure. The viewing ports 18 enable visual inspection of the acetabulum 16 while the shell 12 is seated therein. Finally, when the acetabulum 16 is believed to be properly sized, the instrument 10 is again positioned within the cavity and the peripheral rim 20 of the hemispherical shell 12 is compared to the peripheral boundary of the acetabulum 16. Such comparison may be accomplished by sight and/or by simply running one's finger along the juncture of peripheral rim 20 and the peripheral boundary of acetabulum 16. When the peripheral rim 20 is generally flush with the peripheral boundary of the acetabulum 16, the acetabulum 16 is properly sized for the prosthesis to be fitted therein.

After such determination that acetabulum 16 is properly sized, shell 12 is again seated within the acetabulum 16 and rotated relative thereto by manipulating handle 22. The purpose of this procedure is to locate the best purchase for anchoring holes 30. The surrounding pelvis bone 28 may be viewed along sight lines through bushings 32 until the best proximate anchoring site is found. Relative rotation of shell 12 and handle 22 is prevented by the abutting interaction of slot 40 and key 42. Also, throughout the sizing procedure, handle 22 may be removed from shell 12 which allows shell 12 to remain unattended within the acetabulum cavity 16.

Figure 10:
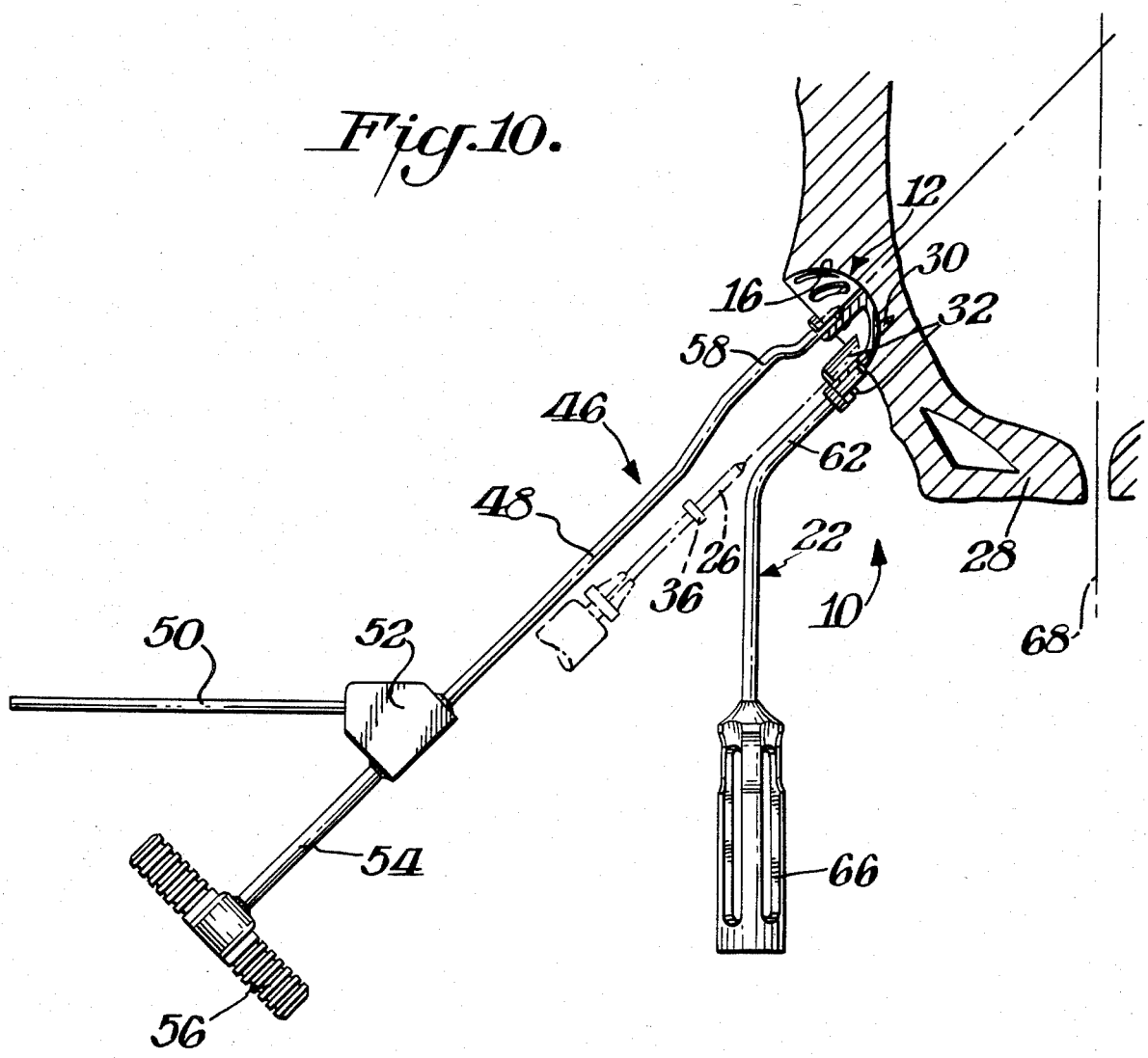
FIG. 10 is a left side elevational view of the acetabulum sizer and drill guide instrument seated within an acetabulum and with the alignment rod attached to the instrument, certain portions being broken away to show interior detail.

Following this procedure, alignment rod 46 is fitted into socket 60 on shell 12 and rotated to a position where offset 58 is opposite the anatomical femur of the patient. Both handle 22 and grip 56 are manipulated until second portion 50 of alignment rod 46 extends laterally of the patient and is also perpendicular to the coronal or long axis 68 of the patient, as shown in FIG. 10. When this alignment occurs, shell 12 is exactly positioned within a 45° lateral opening in acetabulum 16 at neutral anteversion.

The orientation of first portion 48 and its extension 54 of alignment rod 46 is such that first portion 48 and extension 54 form an angle of approximately 45° with the coronal axis 68 of the patient when shell 12 is positioned within a 45° lateral opening in acetabulum 16 at neutral anteversion. Should no anteversion be required, no further alignment of shell 12 is necessary. However, should anteversion be required, shell 12 is rotated the required amount by holding grip 66 and rotating alignment rod 46 the required amount of anteversion while still maintaining the 45° relationship between first portion 48 and its extension 54 relative to coronal axis 68 of the patient. In FIG. 10, shell 12 is positioned at neutral anteversion, and rotation of alignment rod 46 upwardly and out of the plane of the paper produces the desired degree of anteversion.

With shell 12 so positioned, prosthesis anchoring holes 30 are formed in pelvis bone 28 adjacent acetabulum 16. Drill bit 26 is inserted into and through each bushing 32 of drill guide structure 24 and into the pelvis until collar 36 on drill bit 26 engages stop surface 34 on bushing 32. When the first hole is being formed, the tip end portion 38 of handle 22 is fitted within the other bushing 32 and vice versa.

Following this procedure, the acetabulum sizer and drill guide instrument 10 is removed and the prosthesis inserted into the prepared acetabulum cavity 16. The anchoring posts on the prosthesis properly fit within drilled anchoring holes 30. Moreover, the angular orientation of the anchoring holes 30 is such that the prosthesis has the proper amount of anteversion, if desired. When bone cement, such as methyl methacrylate, is used to assist in anchoring the prosthesis within the acetabulum, the properly sized acetabulum results in a uniform distribution of cement between the exterior surface of the prosthesis and the interior surface of the acetabulum.

I claim:

1. An acetabulum sizer adapted for use in implanting an acetabular cup prosthesis, which comprises a substantially hemispherical shell having an outside surface that generally conforms to the outside surface of the prosthesis and a circular peripheral rim, viewing ports in the shell for visual inspection of an acetabulum while the shell is seated therein, and handle means for manipulating the shell relative to the acetabulum.

2. An acetabulum sizer as in claim 1 wherein the viewing ports comprise a series of spaced apart slotted openings positioned around the shell.

3. An acetabulum sizer as in claim 1 including drill guide means on the shell for guiding a drill bit into the pelvis bone adjacent the acetabulum.

4. An acetabulum sizer as in claim 3 wherein the handle means is releasably connected to the drill guide means.

5. An acetabulum sizer as in claim 3 wherein the drill guide means comprises a pair of spaced apart open ended bushings on the shell close to the periphery thereof, each bushing defining a path of travel for the drill bit substantially perpendicular to a plane defined by the peripheral rim of the shell.

6. An acetabulum sizer as in claim 5 wherein the handle means includes a tip end portion constructed and arranged to releasably fit within either one of the bushings, an open ended slot in each bushing, and a key on the outside of the tip end portion constructed and arranged for mating engagement within the slot when the handle is fitted into either one of the bushings whereby relative rotation between the handle means and the shell is prevented.

7. An acetabulum sizer as in claim 5 wherein the bushings are spaced 45° apart.

8. An acetabulum sizer as in claim 5 wherein each bushing includes stop means cooperating with the drill bit for limiting the depth of the holes drilled into the pelvis bone.

9. An acetabulum sizer as in claim 3 including an alignment rod for properly positioning the drill guide means relative to the acetabulum and surrounding pelvis bone, the alignment rod having a first portion constructed and arranged for attachment to the shell, and a second portion connected to the first portion so that the axis of the second portion forms an angle 45° with a plane defined by the peripheral rim of the shell when the first portion is attached to the shell whereby the shell is positioned within a 45° lateral opening in the acetabulum at neutral anteversion when the second portion of the alignment rod extends laterally and is perpendicular to the coronal axis of the person receiving the prosthesis.

10. An acetabulum sizer as in claim 9 including a socket on the inside of the shell constructed and arranged to receive the first portion of the alignment rod.

11. An acetabulum sizer as in claim 1 wherein the handle means includes a proximal end portion having an axis substantially perpendicular to a plane defined by the peripheral rim of the shell, a distal end portion connected to the proximal end portion at an angle of approximately 135°, and grip means on the distal end portion.

12. An acetabulum sizer adapted for use in implanting an acetabular cup prosthesis, which comprises a substantially hemispherical shell having an outside surface that generally conforms to the outside surface of the prosthesis and a circular peripheral rim, drill guide means on the shell for guiding a drill bit into the pelvis bone adjacent the acetabulum, and handle means for manipulating the shell relative to the acetabulum.

13. An acetabulum sizer as in claim 12 wherein the handle means is releasably connected to the drill guide means.

14. An acetabulum sizer as in claim 12 wherein the drill guide means comprises a pair of spaced apart open ended bushings on the shell close to the periphery thereof, each bushing defining a path of travel for the drill bit substantially perpendicular to a plane defined by the peripheral rim of the shell.

15. An acetabulum sizer as in claim 14 wherein the handle means includes a tip end portion constructed and arranged to releasably fit within either one of the bushings, an open ended slot in each bushing, and a key on the outside of the tip end portion constructed and arranged for mating engagement within the slot when the handle is fitted into either one of the bushings whereby relative rotation between the handle means and the shell is prevented.

16. An acetabulum sizer as in claim 14 wherein the bushings are spaced 45° apart.

17. An acetabulum sizer as in claim 14 wherein each bushing includes a stop means cooperating with the drill bit for limiting the depth of the holes drilled into the pelvis bone.

18. An acetabulum sizer as in claim 12 including an alignment rod for properly positioning the drill guide means relative to the acetabulum and surrounding pelvis bone, the alignment rod having a first portion constructed and arranged for attachment to the shell, and a second portion connected to the first portion so that the axis of the second portion forms an angle 45° with a plane defined by the peripheral rim of the shell when the first portion is attached to the shell whereby the shell is positioned within a 45° lateral opening in the acetabulum at neutral anteversion when the second portion of the alignment rod extends laterally and is perpendicular to the coronal axis of the person receiving the prosthesis.

19. An acetabulum sizer as in claim 18 including a socket on the inside of the shell constructed and arranged to receive the first portion of the alignment rod.

20. An acetabulum sizer as in claim 12 wherein the handle means includes a proximal end portion having an axis substantially perpendicular to a plane defined by the peripheral rim of the shell, a distal end portion connected to the proximal end portion at an angle of approximately 135°, and grip means on the distal end portion.

21. A method of preparing an acetabulum prior to implanting an acetabular cup prosthesis therein, which comprises the steps of
removing bone and tissue from the acetabulum until it is properly sized;
periodically positioning a hemispherical shell within the acetabulum, the shell having an outside surface that conforms to the outside surface of the prosthesis and a circular peripheral rim;
viewing the acetabulum through ports in the shell while the shell is positioned therein; and
determining whether the acetabulum is properly sized by comparing the peripheral rim of the shell with the peripheral boundary of the acetabulum, the acetabulum being properly sized when the peripheral rim of the shell is generally flush with the peripheral boundary of the acetabulum.

22. A method of preparing an acetabulum as in claim 21 including the further step of forming prosthesis anchoring holes in the bone surrounding the acetabulum by guiding a hole-forming tool into the bone at an angle perpendicular to the plane defined by the peripheral rim of the shell.

* * * * *